(12) United States Patent
Lawrence et al.

(10) Patent No.: US 6,394,996 B1
(45) Date of Patent: May 28, 2002

(54) SYSTEM FOR ASPIRATING AND IRRIGATING TRACT WOUNDS

(75) Inventors: Matthew Lawrence, Gary, NC (US); Richard Rego, Mansfield, MA (US); Edward F. Doorley, III, East Greenwich, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 601 days.

(21) Appl. No.: 08/779,420

(22) Filed: Jan. 7, 1997

(51) Int. Cl.[7] .................................................. A61M 1/00
(52) U.S. Cl. .................... 604/540; 604/523; 604/43; 604/73
(58) Field of Search ....................... 604/27, 35, 30, 604/39, 40, 43, 54, 73, 93, 280, 275, 266, 902, 19, 48, 514, 93.01, 523, 540–544; 128/139, 156

(56) References Cited

U.S. PATENT DOCUMENTS

| 517,274 A | 3/1894 | Gollings |
|---|---|---|
| 906,711 A | 12/1908 | McHill et al. |
| 1,114,268 A | 11/1914 | Kells |
| 1,178,898 A | 4/1916 | Young |
| 1,188,180 A | 6/1916 | Kells |
| 1,987,907 A | 1/1935 | Jenkins |
| 2,043,630 A | 6/1936 | Raiche |
| 2,199,844 A | 5/1940 | Tucker |
| 2,361,908 A | 11/1944 | Bayers |
| 2,449,497 A | 9/1948 | McLeod |
| 2,614,563 A | 10/1952 | Devine, Jr. |
| 2,804,075 A | 8/1957 | Borden |
| 3,019,447 A | 2/1962 | Sluz |
| 3,065,749 A | 11/1962 | Brass |
| 3,394,705 A | 7/1968 | Abramson |
| 3,430,631 A | * 3/1969 | Abramson .................. 128/350 |
| 3,735,751 A | 5/1973 | Katz |
| 4,002,170 A | 1/1977 | Harsen et al. |
| 4,068,664 A | 1/1978 | Sharp et al. |
| 4,182,385 A | 1/1980 | Williamson |
| 4,400,168 A | 8/1983 | Buechel et al. |
| 4,402,684 A | 9/1983 | Jessup |
| 4,447,226 A | 5/1984 | Mayoral |
| 4,451,257 A | 5/1984 | Atchley |
| 4,468,216 A | * 8/1984 | Muto .......................... 604/43 |
| 4,508,533 A | * 4/1985 | Abramson .................. 604/35 |
| 4,512,765 A | * 4/1985 | Muto .......................... 604/119 |

(List continued on next page.)

FOREIGN PATENT DOCUMENTS

| DE | 195 36 118 A | 4/1996 |
|---|---|---|
| WO | WO 96 25188 A | 8/1996 |

OTHER PUBLICATIONS

Brochure entitled A Debridement System . . . That Won't Leave You All Wet (Zimmer).
Brochure entitled "Spike & Shoot"—Surgilav Plus (Stryker Instruments).
Loehne, Harriett Baugh, "Chapter 17—Pulsatile Lavage with Concurrent Suction", *Wound Care—A Collaborative Practice Manual for Physical Therapists and Nurses*, Aspen Publishers, Inc., pp. 389–398.

*Primary Examiner*—Richard K. Seidel
*Assistant Examiner*—Cris L. Rodriguez
(74) *Attorney, Agent, or Firm*—Kirkpatrick & Lockhart LLP

(57) ABSTRACT

An improved suction and irrigation system for debriding a tract wound includes a suction and irrigation handpiece and a dual lumen suction and irrigation tip that is removably connectible to the handpiece. The tip has a flexible shaft and a connector for connecting the shaft to the handpiece. The flexibility of the shaft facilitates advancement of the shaft to the deepest part of the tract wound while also limiting further trauma to the wound.

15 Claims, 3 Drawing Sheets

U.S. PATENT DOCUMENTS

| | | |
|---|---|---|
| 4,634,435 A | 1/1987 | Ingraham |
| 4,662,871 A | 5/1987 | Rafelson |
| 4,692,140 A | 9/1987 | Olson |
| 4,708,717 A | 11/1987 | Deane et al. |
| 4,759,349 A | 7/1988 | Betz et al. |
| 4,787,894 A | 11/1988 | Turnbull |
| 4,857,047 A | 8/1989 | Amoils |
| 4,915,691 A | 4/1990 | Jones et al. |
| 4,964,849 A | 10/1990 | Robicsek |
| 4,993,941 A * | 2/1991 | Maita et al. .................. 433/80 |
| 5,061,180 A | 10/1991 | Wiele |
| 5,125,902 A | 6/1992 | Berry et al. |
| 5,167,622 A * | 12/1992 | Muto .......................... 604/35 |
| 5,197,949 A | 3/1993 | Anguspanich |
| 5,203,769 A | 4/1993 | Clement et al. |
| 5,224,940 A | 7/1993 | Dann et al. |
| 5,242,386 A | 9/1993 | Holzer |
| 5,248,297 A | 9/1993 | Takase |
| 5,306,237 A * | 4/1994 | Clement et al. .............. 604/30 |
| 5,310,406 A | 5/1994 | Sharpe et al. |
| 5,370,610 A * | 12/1994 | Reynolds ..................... 604/43 |
| 5,380,245 A | 1/1995 | Reiterman et al. |
| 5,395,315 A * | 3/1995 | Griep .......................... 604/35 |
| 5,462,528 A | 10/1995 | Roewer |
| 5,464,390 A | 11/1995 | Arnett et al. |
| 5,496,290 A | 3/1996 | Ackerman |
| 5,499,970 A | 3/1996 | Olson |
| 5,527,276 A * | 6/1996 | Bruce .......................... 604/54 |
| 5,562,640 A | 10/1996 | McCabe et al. |
| 5,795,324 A * | 8/1998 | Morse ......................... 604/27 |

\* cited by examiner

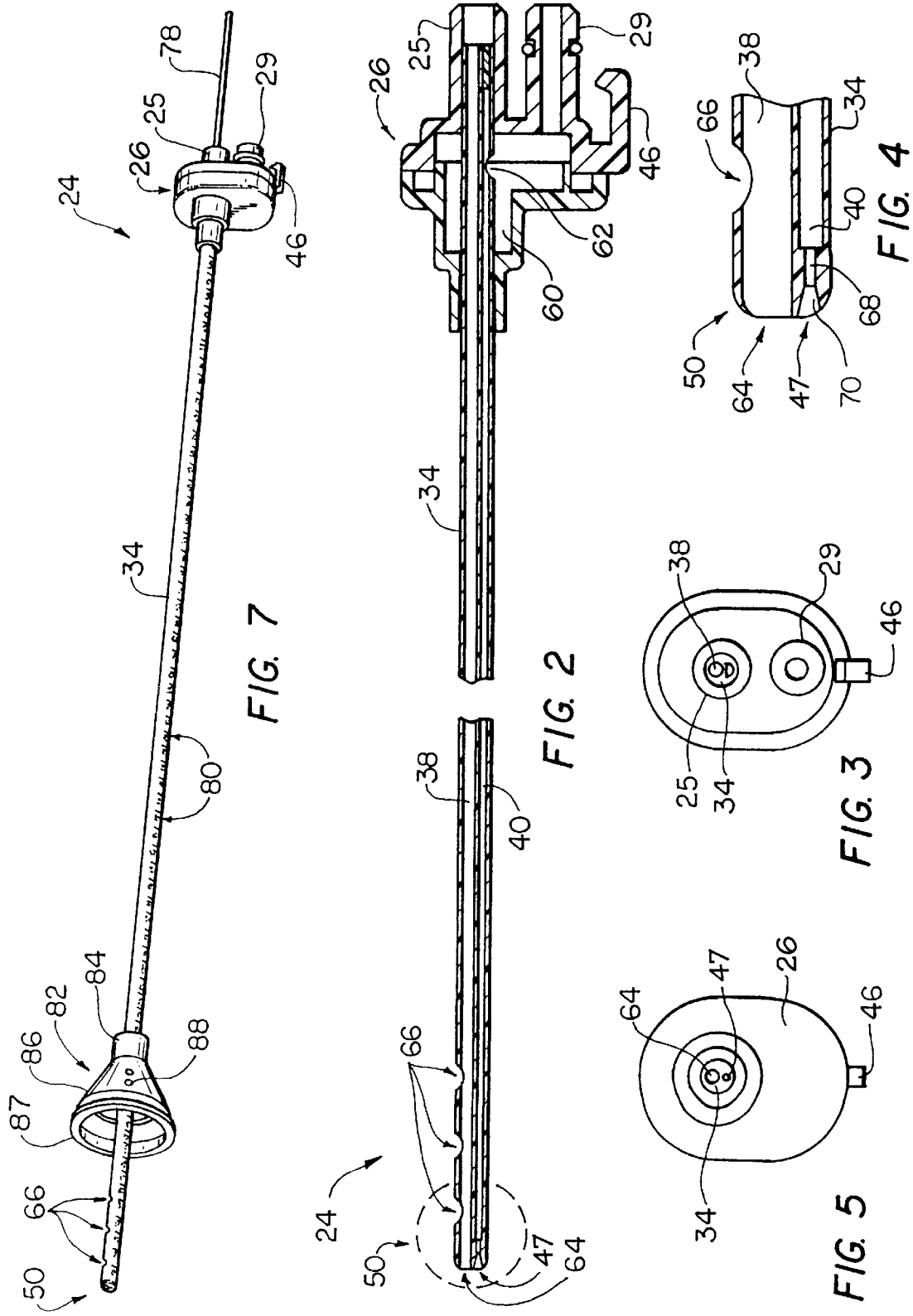

SYSTEM FOR ASPIRATING AND IRRIGATING TRACT WOUNDS

FIELD OF THE INVENTION

This invention relates to systemic irrigation of a tract wound.

BACKGROUND OF THE INVENTION

A tract wound is an externally accessible, elongated wound in the soft tissue of the body, often the result of a progressively developing infection. When the skin is broken, as by a cut or an external ulcer, and infection develops, the infection can proliferate randomly through the tissue to form a bending, tortuous tunnel. Tract wounds are a common post-surgery complication, particularly after open-chest surgery. It is important that a tract wound be debrided with an antiseptic solution promptly upon discovery to prevent the infection from spreading so that the wound can heal. Tract wounds also are common with patients having poor circulation, hepatitis, AIDS or other conditions in which the patient's ability to overcome the infection is subnormal.

Tract wounds typically are treated by physical therapists. Among the procedures for treating tract wounds involves simply bathing the patient in a whirlpool bath. That procedure is generally ineffective, particularly with relatively deep tract wounds, because the bath water usually cannot reach the deepest part of the wound where infectious material resides and can proliferate.

In another procedure, intended to treat the deep region of the wound a rigid elongate tip of a bulb syringe, filled with irrigation liquid, is inserted into the tract wound and is advanced until significant resistance is felt by the therapist. The resistance may suggest to the therapist that the tip is positioned at the deepest part of the wound. The bulb then is squeezed to force irrigation liquid into the tract wound. Debris and spent irrigation liquid may be withdrawn through the rigid tip when the bulb expands.

In still another similar irrigation procedure, a rigid tip having suction and irrigation lumens is advanced through the tract wound until significant resistance is felt. Irrigation liquid then may be delivered from an external reservoir, through the irrigation lumen into the wound. The suction lumen is connected to a suction source to simultaneously withdraw debris and spent irrigation liquid from the wound.

Although a significant improvement over the whirlpool procedure, the latter procedures may not effectively remove infectious material and other debris from the deep regions of a tortuous tract wound because the stiff tip cannot be maneuvered past the sharp bends. Resistance to tip advancement caused by the bends may be mistaken by the therapist to indicate that the tip is positioned at the deepest part of the wound. Consequently, infectious debris may remain in the deepest region of the wound, enabling the infection to proliferate and make the wound even deeper. Another difficulty with the use of the above tips is that the interior walls of a tortuous tract wound may be further traumatized when the tip is forced through the wound. Moreover, where the patient usually is awake during such procedures, such trauma may cause significant discomfort.

It would be desirable to provide an irrigation device and procedure that may effectively debride the deeper parts of a tract wound, including tortuous wounds. It also would be desirable for that device to be used without causing further tissue trauma and discomfort to the patient. It is among the overall objects of the invention to provide such a devices and methods.

SUMMARY OF THE INVENTION

The invention includes an elongate, flexible suction and irrigation tip, about four about sixteen inches long, constructed to facilitate advancement to the deepest part of a tortuous tract wound. To that end, the tip includes a flexible shaft having a suction lumen, an irrigation lumen, and a connector to detachably connect the tip to a handpiece. The material and geometry of the shaft cooperate to enable the tip to be navigated to the deepest part of a tortuous tract wound without kinking or otherwise adversely affecting flow through the lumens. The flexible shaft is formed to bend to a small radius without adversely affecting flow through either lumen.

In those instances, when a rigid tip is desirable, a rigid obturator may be inserted into the suction lumen through the proximal end of the tip, and the assembly of tip and obturator may be inserted into the tract wound. After the tip has been positioned in the wound, the obturator is removed from the tip suction lumen. The tip then is connected, at its proximal end, to the handpiece. The obturator also may be inserted into the suction lumen through the distal end to clear obstructions that may develop within the suction lumen.

It is among the general objects of the invention to provide an irrigation and debridement device that facilitates advancement to the deepest part of a tract wound, including, particularly a tract wound having a tortuous path.

It is among the general objects of the invention to provide an irrigation and debridement device and method that efficiently removes infectious debris from a tract wound.

It is another object of the invention to provide an irrigation and debridement device and method for tract wounds that is less likely to cause discomfort to a patient than the prior devices.

DESCRIPTION OF THE DRAWINGS

The foregoing and other objects and advantages of the invention will be appreciated more fully from the following further description thereof, with reference to the accompanying drawings wherein:

FIG. 2 is a longitudinal cross-sectional view of the tip as seen along the line 2—2 of FIG. 1;

FIG. 3 is a rear view of the suction and irrigation tip as seen from 3—3 of FIG. 2;

FIG. 4 is an enlarged cross-section of the distal end of the tip shown in FIG. 2;

FIG. 5 is a front view of the suction and irrigation tip as seen from 5—5 of FIG. 2;

FIG. 7 is perspective view of a flexible tip having depth indicia and a splash shield.

DESCRIPTION OF THE ILLUSTRATIVE EMBODIMENT

Figure 1:
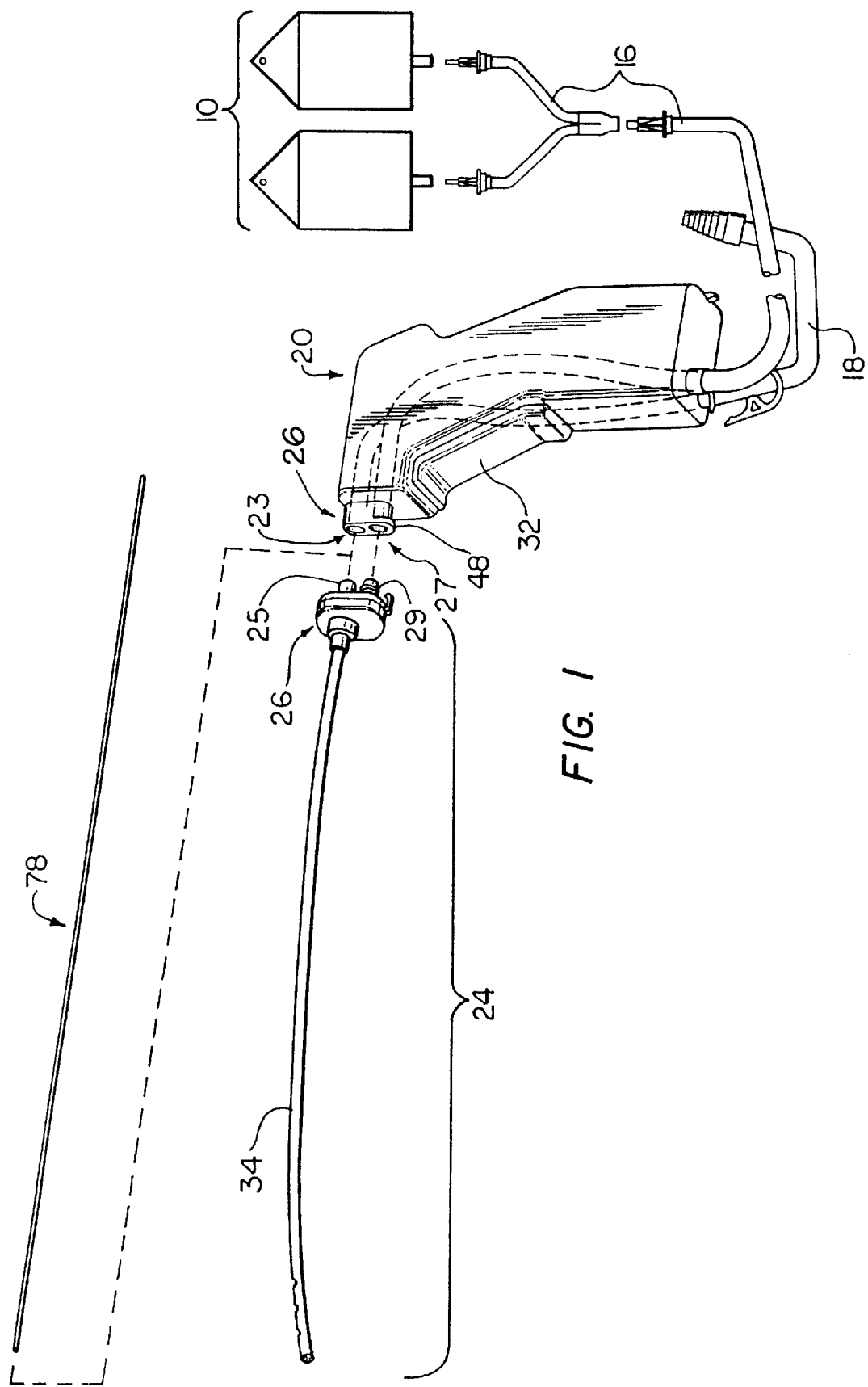
FIG. 1 is an illustration of a suction and irrigation system in accordance with the invention.
Figure 6C:
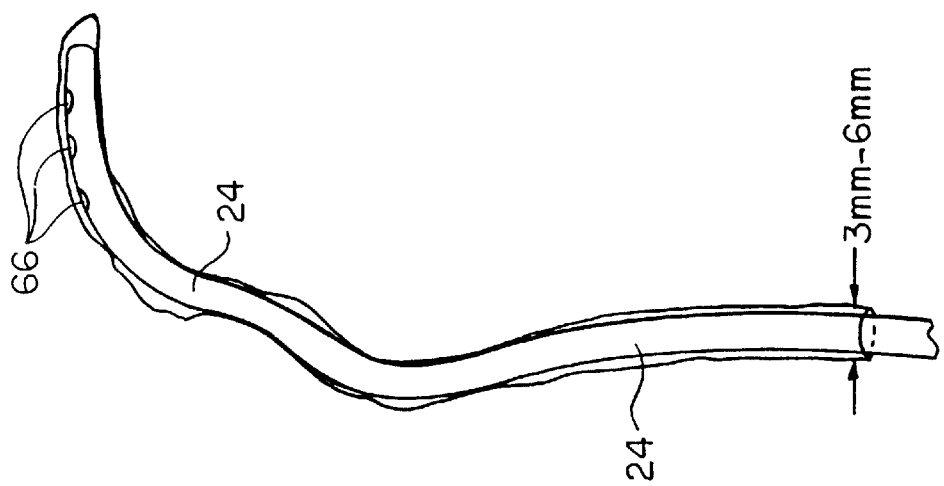
FIGS. 6A, 6B and 6C are diagrammatic illustrations of a tortuous tract wound showing placement of a prior art device and of the invention in the wound.

FIG. 1 shows a system for irrigating and aspirating a tract wound, including a deep, tortuous wound W as illustrated diagrammatically in FIG. 6. The tract wound typically may have a transverse dimension of three millimeters to six millimeters, the larger wounds typically having remained untreated for a longer period of time. The wound may be up to about six to eight inches deep, or more, depending on a number of factors. The system includes a reservoir 10 containing irrigation liquid, such as saline. The reservoir is connected by tubing 16 that extends to and is associated with a handpiece 20 by which the delivery of irrigation liquid can be controlled. The handpiece 20 also is associated with tubing 18 that is connectible to a source of suction (not shown). The handpiece is detachably connectible to an elongate tip 24 that is adapted to be inserted into the tract wound. The tip 24 includes two lumens that extend the full length of the tip, including an irrigation lumen through which irrigation liquid is delivered and a suction lumen through which spent irrigation liquid and biological debris can be aspirated from the tract wound.

Although the handpiece 20 may take any desired configuration, the invention is illustrated in connection with a preferred handpiece such as that disclosed in co-pending U.S. patent application Ser. No. 08/389,155 filed Feb. 5, 1995 (Pasch et al.), the entire disclosure of which is hereby incorporated by reference. As disclosed in further detail in that application, the handpiece includes a self-contained pump mechanism, batteries for driving the pump mechanism and a control system for controlling the flow of liquid through the system. The handpiece 20 may be somewhat pistol shaped and has a connector fitting 22 at one end that can be detachably coupled to a fitting 26 on the proximal end of the tip 24.The connector fitting 22 includes a suction port 23 and an irrigation port 27 that mate with corresponding suction and irrigation ports 25, 29 on the tip fitting 26. The fittings 22, 26 are constructed to communicate irrigation liquid to the irrigation lumen in the tip and suction to the suction lumen of the tip. Reference is made to the application Ser. No. 08/389,155 for the details of the fittings 22, 26. The handpiece 20 includes a trigger 32 that, when squeezed, closes electrical contacts within the handpiece to initiate operation of the pumping mechanism (not shown) within the handpiece. The pumping mechanism preferably is constructed to develop a pulsatile liquid stream.

As shown in FIG. 2, the tip 24 includes a flexible shaft 34, preferably extruded from a low durometer (e.g., 85 Shore-A) plasticized polyvinyl chloride. The shaft 34 is extended to form a suction lumen 38 and a parallel irrigation lumen 40 that extend side by side within the shaft. The tip suction lumen 38 preferably is circular in cross-section to maximize its flow area to reduce the risk of it becoming clogged with debris from the wound. The cross-section of the irrigation lumen 40 is not as critical and may be semi-circular or crescent-shaped. The irrigation lumen 40 may have a smaller cross-sectional flow area that can be compensated for by increasing the inlet pressure at the inlet end of the lumen 40. The shaft 34 also includes a plurality of suction holes 64 and 66, a rounded, atraumatic distal end 50 to minimize trauma to the wound as the tip 24 is advanced through the tract wound, and a liquid outlet nozzle at the distal end of the shaft for emitting irrigation liquid from the irrigation lumen 40.

In the preferred embodiment, the connector 22 includes male suction and irrigation ports 25 and 29 that are insertable into the suction and irrigation ports 23 and 27 on the handpiece fitting 22. The fitting 26 also includes a clip 46 to detachably connect to a depending lip 48 on the fitting 22. In order to avoid unnecessary bends in the suction lumen 38, the tip fitting 26 is formed to include a chamber 60 that surrounds the proximal end of the shaft 34 so that the shaft can pass straight through the chamber to the suction ports 23. The chamber 60 communicates with the irrigation ports 25 and the irrigation lumen 40 through a liquid port 62 formed in that portion of the shaft disposed within the chamber 60; When connected to the handpiece 20, the tip suction lumen 38, suction ports 25, and suction lumen associated with the handpiece define a flow path for directing aspirated debris and spent irrigation liquid from the wound. Similarly, the tip irrigation lumen 40, irrigation ports 25, irrigation lumen associated with the handpiece, and liquid delivery tube 16 together form a flow path for directing irrigation liquid from the reservoir to the tract wound.

The suction holes 64 and 66 include an end hole 64 at the distal end of the tip and three longitudinally spaced side holes 66 formed through the wall of the shaft 34. The multiple holes distribute the suction over a large area to produce a gentle suction at each of the holes 64 and 66. That reduces the likelihood that the shaft 34 will undesirably attach to body tissue. In the event that one or more of the suction holes 64 and 66 becomes clogged with debris, the strength of the aspiration through the remaining holes will increase proportionally. In the preferred embodiment, the end hole 64 may have a diameter of about 0.09 inch, and the three longitudinally aligned holes 66 may be elliptically shaped, having a major dimension of about 0.170 inch, and a minor dimension of about 0.150 inch.

As shown in FIG. 4, the outlet orifice 47 may be configured to emit irrigation liquid in a conical spray pattern to maximize the area of the tract wound that is debrided. Preferably, the stagnation pressure of emitted irrigation liquid from the tip is up to about 15 p.s.i., that being the generally accepted standard maximum stagnation pressure for wound treatment. Of course, when the device is used, the therapist may adjust the pump pressure to control and vary the stagnation pressure to accommodate the particular clinical situation. The preferred conical pattern and stagnation pressure may be achieved with an outlet nozzle having a cylindrical lumen 68,and a conical emission orifice 70. In the preferred embodiment, the cylindrical lumen 68 may have a diameter of about 0.035 inch. The frustoconical orifice 70 diverges at an angle of about 20° diameter of about 0.045 inch. The device is used in connection with a pump, preferably pulsatile, that can develop a stagnation pressure of the emitted irrigation liquid of up to about 15 p.s.i.

Figure 6B:
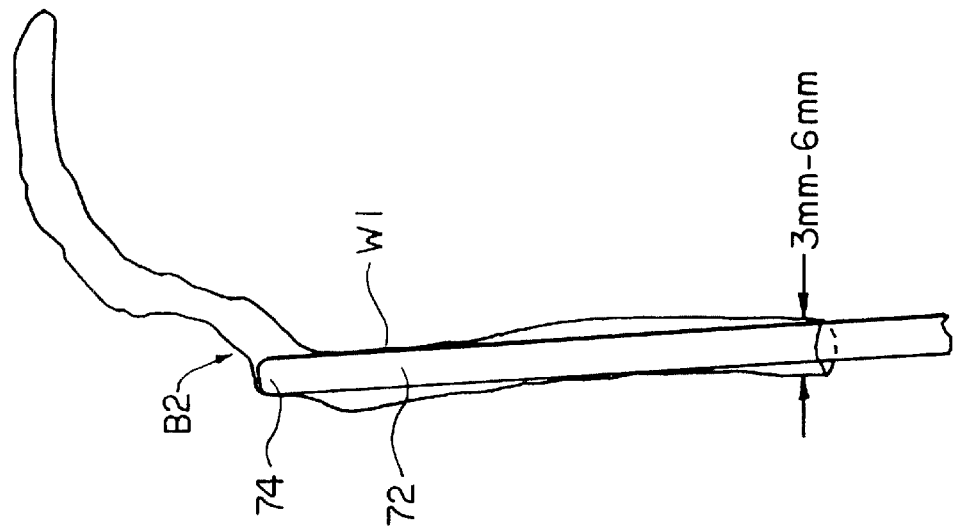
Figure 6A:
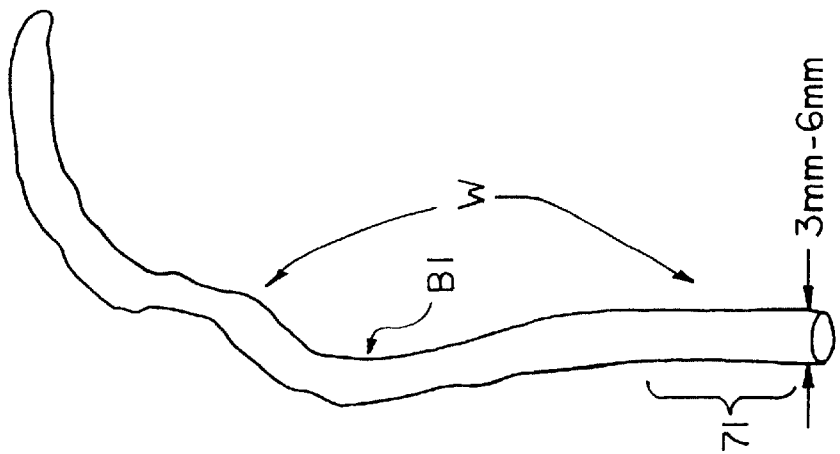

The shaft 34 is constructed so that it has sufficient column strength to permit it to be pushed from its proximal end into and through the tract wound in combination with sufficient longitudinal flexibility so that it can conform to bends, including bends of a tortuous tract wound. A representative tortuous tract wound W is shown in FIG. 6A having an entry segment 71 leading from the skin and following an unpredictable path through the patient's tissue. FIG. 6A illustrates the random configuration of the tract wound, including relatively straight segments as well as bends, some of which may be relatively sharp, of the order of 20° or as much as about 90°. Additionally, it should be understood that although FIG. 6A necessarily is two dimensional, tract wounds are not so limited and proliferate in three dimensions. FIG. 6B shows, diagrammatically, the consequences of inserting a conventional tract wound irrigator having a relatively stiff construction. The irrigator 72 may advance into the relatively straight portion at the entry end of the wound. It may encounter relatively gradual bends, as shown at B1, in FIG. 6A and may be advanceable past through such bends by forcing tissue out of the way as suggested at W1 in FIG. 6B. When a relatively sharp bend is encountered, as suggested at B2 in FIG. 6B, it may not be possible to continue advancement of the tip. The abutment of the distal end 74 of the tip with the bend B2 in the wound W may be taken, mistakenly, by the therapist as an indication that the deepest part of the wound has been reached. Consequently, the more distal portions of the tortuous tract wound may remain essentially untreated. Should the therapist attempt to force the tip further, that likely would result in significant trauma and patient discomfort.

In contrast with the prior art devices, the present invention enables the shaft of the tip to be advanced through the tortuous tract wound W, the shaft being sufficiently flexible to bend without causing significant trauma or pain for the patient. In the above example, when advancing the present invention through the wound W to the bend B2, the therapist may continue to push on the proximal end of the shaft even after the distal end has contacted the first significant bend B2 at which advancement of the prior art device 72 may have been terminated. The shaft embodied in the present invention is sufficiently flexible so that even after the tip has engaged a wall of a sharp bend B2, the shaft will tend to flex to conform to the configuration of the bend. In some instances, the therapist may apply a combination of longitudinal and rotational motion to facilitate the distal end of the shaft following the configuration of the wound W. In that manner, the device can be advanced and navigated through a tortuous tract wound to increase the probability that the distal end of the device will reach fully to the deepest part of the tract wound.

In accordance with the invention, the shaft 34 preferably is manufactured from a relatively soft, flexible polymeric material, such as polyvinyl chloride (PVC). Other suitable polymers may be used. The shaft is between about four to sixteen inches in length, having an outer transverse cross-sectional dimension of between about 9 and 18 French (i.e. 0.117 to 0.234 inch). The balance between the amount of the cross-sectional area of the shaft that comprises polymer and lumen is a significant factor in the ability of the device to perform satisfactorily with tortuous tract wounds. Preferably, the cross-sectional area defined by the suction and irrigation lumens should comprise between about 30 to 60 percent of the total cross-sectional area of the shaft., The shaft materials should have a durometer of between about 70–90 Shore-A, a modulus of elasticity of between about 1,000–2,000 p.s.i., and a specific gravity of between about 1.05–1.35 grams per cubic centimeter. More preferably, the shaft should have a durometer on the order of about 85 Shore-A, a modulus of elasticity on the order of about 1,500–1,600 p.s.i., and a specific gravity on the order of about 1.1–1.25 grams per cubic centimeter.

The shaft preferably has the ability to bend to a minimum radius without kinking to adversely affect flow through the lumens. The geometry, material and dimensions of the tip are such that the desired stagnation pressure can be maintained under the influence of a predetermined liquid inlet pressure even when the tip is bent. Preferably, the shaft is sufficiently flexible so that it can bend through at least an angle of about 90° without any substantial drop in the stagnation pressure of the emitted liquid. Such bending radius may vary from about one-quarter inch for a 9 French shaft (0.117 inch) to about five-eighths inch for an 18 French (0.234 inch) shaft.

In some cases, it may be desirable to have the ability to stiffen the tip. To that end, as shown in FIGS. 1 and 7, the system also may include a relatively rigid obturator 78 that is insertable into the proximal end of the tip suction lumen 38. The obturator 78, which may be made from a rigid polymer such as polycarbonate, preferably has a cross-sectional diameter slightly less than that of the suction lumen 38 so that it will be easily slidable through the shaft. By way of example, for use with a suction lumen 0.090 inches in diameter, an obturator having a diameter of about 0.070 inch and a length about one inch longer than that of the tip (e.g., about five to seventeen inches). With the obturator assembled with the tip, the assembly can be advanced and manipulated, as desired, into and through the tract wound. The obturator may be partially or fully withdrawn to permit a portion or all of the shaft to have its desired flexibility. When the device has been placed with the assistance of the obturator and its placement is complete, the obturator may be removed and the fitting 26 connected to the fitting 22 on the handpiece. The irrigation and aspiration procedure then may be completed. The obturator 78 also may be inserted into the distal end of the suction lumen to remove blockage through that lumen.

FIG. 7 also shows visual indicia 80, on the outer surface of the shaft 34, that indicates the depth to which the shaft 34 has been inserted into the tract wound. This indicia 80 preferably is graduated in one centimeter increments. A radiopaque stripe (not shown) also may be longitudinally extruded on the outer surface of the shaft 34 to enable the shaft 34 to be visible under x-rays.

In a modified embodiment, a flexible splash shield 82 (FIG. 7) is slidably mounted to the shaft 34 to reduce splash back from the tract wound. The splash shield 82 includes a proximal collar 84 and a conical body 86 that diverges in a distal direction to a distal rim 87. A plurality of circumferential ridges (e.g., three, not shown) may be included on the inner surface of the shield 82 to serve as cutting guides for cutting the shield 82. Vent holes 88 formed in the side of the shield 82 prevent the shield 82 from collapsing under suction and also enable air to mix with the debris aspirated from the site to avoid stagnation of debris within the shield 82. The shield 82 may be made from a flexible, substantially clear plastic that may be shaped during use to conform to the shape and contour of the irrigation site.

When in use, the irrigation system is assembled by connecting the tip 24 to the handpiece 20, the flexible suction tube connector 30 to a suction source, and the flexible liquid delivery tubing 16 between the handpiece irrigation lumen 28 and the reservoir 10. After assembly, the tip 24 is inserted into the tract wound and slowly advanced through the tract wound toward the deepest part of the wound. The internal walls of the tract wound guide the tip 24 through the path of the tract wound. When resistance is felt, the therapist may gently rotate the handpiece 20 and apply slightly more longitudinal force to ascertain whether the resistance is caused by either a bend in the wound or the deepest part of the wound. The tip 24 should be advanced further if the therapist determines that the resistance is caused by a bend. The shaft may bend and flex easily, thus facilitating advancement to the deepest parts of even a tortuous tract wound. Once the tip 24 is properly positioned in the tract wound, the attendant may depress the handpiece trigger 32 to pump irrigation liquid into the wound and aspirate spent irrigation liquid, infection, biological matter, and other debris from the wound. Both the tip 24 and handpiece 20 should be discarded after use.

From the foregoing, it should be appreciated that the invention provides an improved suction and irrigation device for use in debriding tract wounds. The system should debride a tortuous tract wound more efficiently and with less wound trauma than prior art tract wound debridement devices. It should be understood, however, that the foregoing description of the invention is intended merely to be illustrative thereof and that other embodiments and modifications may be apparent to those skilled in the art without departing from its spirit.

Having thus described the invention what we desire to claim and secure by Letters Patent is:

1. A tract wound irrigation tip comprising:
    an elongate flexible shaft having a proximal end, a distal end, a suction lumen and an irrigation lumen, the suction and irrigation lumens extending through the shaft and being open at the distal end of the shaft;
    a connector at the proximal end of the shaft for connecting the suction lumen to a source of suction and the irrigation lumen to a source of liquid under pressure;
    the shaft being sufficiently longitudinally flexible to be bendable along its length, including its distal end, to a radius at least as small as about ⅝ inch without kinking, whereby the tip may be navigated through a tract wound to effect irrigation of the tract wound.

2. The wound irrigation tip as defined in claim 1 wherein the suction and irrigation lumens extend in side-by-side relation.

3. The wound irrigation tip as defined in claim 1 wherein the distal end of the shaft has a plurality of longitudinally spaced side holes formed therein in communication with the suction lumen, the suction lumen terminating in an end hole at the distal extremity of the tip.

4. The wound irrigation tip as defined in claim 1 further comprising:
    the distal end of the irrigation lumen defining an outlet nozzle configured to emit liquid in a conical pattern.

5. The wound irrigation tip as defined in claim 1 wherein the shaft is between four inches to about sixteen inches long, the cross-sectional flow area of the suction lumen is substantially larger than the cross-sectional area of the irrigation lumen.

6. The wound irrigation tip as defined in claim 1 further comprising, an obturator dimensioned to be slidably receivable in the suction lumen, the obturator being insertable into the suction lumen from either end of the shaft and being longer than the shaft.

7. The wound irrigation tip as defined in claim 6 wherein the obturator has substantially greater longitudinal stiffness than the shaft.

8. The wound irrigation tip comprising:
    an elongate flexible shaft having a proximal end, a distal end, and suction and irrigation lumens extending through the shaft;
    a connector at the proximal end of the shaft for connection of the irrigation lumen to a liquid pressure source;
    the irrigation lumen terminating at its distal end at an outlet, the geometry and dimensions of the irrigation lumen and outlet being configured so that the stagnation pressure of liquid emitted from the outlet is at a selected magnitude under the influence of a predetermined liquid inlet pressure;
    the shaft being sufficiently flexible to enable it to bend through at least an angle of 90° without any substantial drop in the stagnation pressure of the emitted liquid.

9. The tract wound irrigation tip as defined in claim 8 wherein the radius of the bend is at least as small as about ⅝ inch.

10. The wound irrigation tip comprising:
    an elongate flexible shaft having a proximal end, a distal end and suction and irrigation lumens extending through the shaft, the shaft being between about four to about sixteen inches long, having an outer diameter of about 9 French to about 18 French, a modulus of elasticity between about 1,000 p.s.i. to about 2,000 p.s.i., a specific gravity between about 1.05 grams per cc to about 1.25 grams per cc and a durometer between about 70 Shore A to about 90 Shore A;
    the area defined by the lumens comprising between about 30% to about 60% of the cross-sectional area of the shaft.

11. The tract wound irrigation tip as defined in claim 10 further comprising the durometer being about 85 Shore A, the modulus of elasticity being about 1,500 to about 1,600 p.s.i. and the specific gravity being about 1.1 to about 1.25 grams per cc.

12. A device for irrigating and aspirating a tract wound comprising:
    a tract wound irrigation tip as defined in either of claims 1 or 10;
    a handpiece having a suction lumen and an irrigation lumen associated therewith;
    a connector on the handpiece detachably connectible to the connector at the proximal end of the shaft for cooperatively connecting the suction and irrigation lumens of the shaft and the handpiece; and
    the handpiece having control elements operatively associated with its irrigation lumen to control flow of irrigation liquid to the shaft.

13. The device as defined in claim 12 further comprising a pump in fluid communication with the irrigation lumen, for developing pulsatile liquid flow through the irrigation lumen.

14. A method for irrigating a tract wound comprising:
    providing an elongate flexible shaft having a proximal end, a distal end, a suction lumen and an irrigation lumen, the suction and irrigation lumens extending through the shaft and being open at the distal end of the shaft; and
    advancing the flexible shaft into and through the tract wound, the shaft being sufficiently flexible to enable it to bend through/at least an angle of 90° at a radius at least as small as five-eighths of an inch without adversely affecting the functioning of the lumens.

15. The method as defined in claim 14 further comprising:
    advancing the shaft to place its distal extremity at the distal end of the tract wound to enable liquid emitted from the distal end of the shaft to be directed at the distal end of the wound.

* * * * *

UNITED STATES PATENT AND TRADEMARK OFFICE
CERTIFICATE OF CORRECTION

PATENT NO. : 6,394,996 B1
DATED : May 28, 2002
INVENTOR(S) : Lawrence et al.

It is certified that error appears in the above-identified patent and that said Letters Patent is hereby corrected as shown below:

<u>Title page,</u>
Item [75], add fourth inventor -- Harriet B. Loehne --.

Signed and Sealed this

Fifteenth Day of July, 2003

JAMES E. ROGAN
*Director of the United States Patent and Trademark Office*